US00PP10792P

United States Patent [19]

Manten

[11] Patent Number: Plant 10,792

[45] Date of Patent: Feb. 16, 1999

[54] AZALEA PLANT NAMED 'SAYONARA'

[76] Inventor: Heinz Manten, Heideweg 53, 47608 Geldern, Germany

[21] Appl. No.: 929,489

[22] Filed: Sep. 15, 1997

[51] Int. Cl.[6] ..... A01H 5/00

[52] U.S. Cl. ..... Plt./56

[58] Field of Search ..... Plt./55, 56

[56] References Cited

U.S. PATENT DOCUMENTS

P.P. 10,523 7/1998 Stahnke et al. ..... Plt./56

*Primary Examiner*—Howard J. Locker
*Assistant Examiner*—Kent L. Bell
*Attorney, Agent, or Firm*—C. A. Whealy

[57] ABSTRACT

A new and distinct cultivar of Azalea plant named 'Sayonara', characterized by its spreading, arching and freely branching growth habit; attractive semi-double, pink-colored flowers with dark purple-spotted/speckled centers; and good postproduction longevity.

2 Drawing Sheets

The present invention relates to a new and distinct cultivar of Azalea, botanically known as *Rhododendron simsii,* and hereinafter referred to by the cultivar name 'Sayonara'.

The new cultivar is a product of a planned breeding program conducted by the inventor in Geldern, Germany. The objective of the breeding program is to create new Azalea cultivars that grow rapidly and have uniform plant habit and attractive flower colors. The new cultivar originated from a cross made by the inventor of the nonpatented cultivar 'Knut Erwin' as the male, or pollen, parent with the nonpatented cultivar 'Heursel' as the female, or seed, parent. The cultivar 'Sayonara' was discovered and selected by the inventor as a seedling within the progeny of the stated cross in a controlled environment in Geldern, Germany, in 1989. Plants of the new Azalea were first flowered in 1991.

Compared to plants of the male parent, the red-flowered cultivar 'Knut Erwin', plants of the new Azalea flower earlier and are less woody. Compared to plants of the female parent, the lilac-flowered cultivar 'Heursel', plants of the new Azalea grow faster and flower earlier.

Asexual reproduction of the new cultivar by terminal cuttings taken at Geldern, Germany, has shown that the unique features of this new Azalea plant are stable and reproduced true to type in successive generations of asexual reproduction.

The following traits have been repeatedly observed and are determined to be the unique characteristics of 'Sayonara'. These characteristics in combination distinguish the new Azalea plant as a new and distinct cultivar:

1. Spreading and arching growth habit.
2. Very freely branching.
3. Attractive semi-double, pink-colored flowers with dark purple-spotted/speckled centers.
4. Good postproduction longevity.

Plants of the new Azalea can be compared to plants of the cultivar 'Gloria' (not patented). However in side-by-side comparisons in Geldern, Germany, under commercial practice, plants of the new Azalea are more compact and flower earlier than plants of the cultivar 'Gloria'.

Plants of the new Azalea can also be compared to plants of the cultivar 'Lara' (not patented). However in side-by-side comparisons in Geldern, Germany, under commercial practice, plants of the new Azalea have a more compact growth habit and longer postproduction longevity.

Plants of the new Azalea can also be compared to plants of the new Azalea's sibling cultivar 'Wendy' (disclosed in U.S. Plant patent application Ser. No. 08/923,727). However in side-by-side comparisons conducted in Geldron, Germany, and Salinas, Calif., under commercial practice, plants of the new Azalea differed from plants of the cultivar 'Wendy' in the following characteristics:

1. Plants of the new Azalea are more horizontally spreading than plants of the cultivar 'Wendy'.
2. Plants of the new Azalea are shorter than plants of the cultivar 'Wendy'.
3. Lateral branches of plants of the new Azalea are narrower and less rigid than lateral branches of plants of the cultivar 'Wendy'.
4. Plants of the new Azalea have shorter leaves than plants of the cultivar 'Wendy'.
5. Plants of the new Azalea have slightly smaller flowers than plants of the cultivar 'Wendy'.
6. Patal margins of plants of the new Azalea are more ruffled than petal margins of plants of the cultivar 'Wendy'.
7. Petal color of plants of the new Azalea is lavender pink whereas petal color of plants of the cultivar 'Wendy' is reddish pink.

The new Azalea plant has not been observed under all possible environmental conditions. The phenotype may vary significantly with variations in environment such as temperature, light level, nutrition and water status without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The first sheet of photographs comprises a side perspective view of a typical plant of 'Sayonara'.

The second sheet of photographs comprises a close-up view of typical flowers of 'Sayonara'. Flower and foliage colors in the photographs may appear different than the actual colors due to light reflectance.

DETAILED BOTANICAL DESCRIPTION

The following observations, measurements and values describe plants grown in Salinas, Calif., in 12.5-cm containers under glass with day temperatures ranging from 24° to 27° C., night temperatures ranging from 13° to 16° C., and light levels averaging 4,500 footcandles.

In the following description, color references are made to The Royal Horticultural Society Colour Chart except where general terms of ordinary dictionary significance are used.

Botanical classification: *Rhododendron simsii* cultivar 'Sayonara'.

Parentage:

*Male or pollen parent .—Rhododendron simsii* cultivar 'Knut Erwin', not patented.

*Female or seed parent.—Rhododendron simsii* cultivar 'Heursel', not patented.

Propagation:

*Type*.—By terminal cuttings.

*Time to initiate roots*.—20 to 25 days at temperatures of 23° C. depending on season.

*Time to develop roots*.—45 to 55 days at temperatures of 23° C. depending on season.

*Rooting habit*.—Vigorous and finely-branched.

Plant description:

*Plant form and growth habit*.—Perennial, evergreen, horizontal, spreading and outwardly arching, wide inverted triangle. Moderate vigor.

*Branching habit*.—Dense, very freely branching, about five lateral branches develop after removal of terminal apex.

*Plant height, soil level to top of flowers*.—About 10 cm.

*Plant diameter, area of spread*.—About 28 cm.

*Lateral branch description*.—Length: About 11 cm. Diameter: About 3 mm. Color: Immature: 145A. Mature: 166B. Texture: Moderately pubescent. Pubescence: Brown in color.

Foliage description:

*Arrangement*.—Alternate, single.

*Leaf size, largest leaves*.—Length: About 4.5 cm. Width: About 2 cm.

*Leaf shape*.—Elliptic to oblanceolate.

*Leaf apex*.—Mucronate.

*Leaf base*.—Cuneate.

*Margin type*.—Entire.

*Texture*.—Durable, leathery, slightly glossy, both surfaces moderately pubescent.

*Color*.—Young foliage, upper surface: 137A. Young foliage, lower surface: 138A. Mature foliage, upper surface: Darker than 147A. Mature foliage, lower surface: 137C.

*Petiole*.—Length: About 1 cm. Diameter: About 1 mm. Color: 138A/138B.

Flower description: *Natural flowering season*.—Spring after sufficient cool period, forced into flowrer year round.

*Flower appearance and arrangement*.—Semi-double pink flowers with dark purple-speckled/spotted centers. Flowers arranged singly at terminals with usually five to seven flowers per terminal, freely flowering. Flowers face outward. Flowers persistent.

*Flower diameter*.—About 7 cm.

*Flower longevity*.—Four to six days depending on temperature.

*Flower bud*.—Rate of opening: About three days depending on temperatures. Length: About 2.3 cm. Diameter: About 1 cm. Shape: Ovoid. Color: 70C with green margins.

*Petals*.—Appearance: Satiny, smooth, ruffled at margins. Texture: Glabrous. Arrangement: Semi-double. Outer corolla consists of five fused petals and inner corolla consists of up to 5 irregularly-shaped fused stamenoidal petaloids. Shape: Elliptic to rounded. Apex: Rounded. Margin: Serrulate and ruffled. Length: About 4.5 cm. Width: About 3 cm. Color: When opening, upper surface: 70B with spots/speckles, 59B, at base of lower three petals. When opening, lower surface: 75A/75B with white, 155B, at midvein. Fully opened, upper surface: 75A with spots/speckles, 59B, at base of lower three petals. Fully opened, lower surface: 75A/75B fading to white, 155D, at midvein.

*Sepals*.—Appearance: Five sepals fused into a star-shaped calyx. Texture: Pubescent. Shape: Lanceolate. Apex: Acute. Margin: Entire. Color, upper and lower surfaces: 145A.

*Peduncles*.—Length: About 1.2 cm. Angle: Upright. Strength: Rigid. Color: 145A, pubescent.

*Reproductive organs*.—Androecium: Stamen number: About five, some fused into petaloids. Anther shape: Oblong. Anther size: About 2 mm. Anther color: Dark pink. Amount of pollen: Low. Gynoecium: Stigma shape: Rounded. Stigma diameter: About 1 mm. Stigma color: Green becoming yellow with development. Style length: About 2.2 cm. Style color: White to light pink. Ovary color: Green.

Disease resistance: No known Azalea diseases observed to date on plants grown under commercial greenhouse conditions. Plants of the new Azalea appear to be less susceptible to diseases than other commercial cultivars.

Seed production: Seed production has not been observed. PS

It is claimed:

1. A new and distinct Azalea plant named 'Sayonara', as illustrated and described.

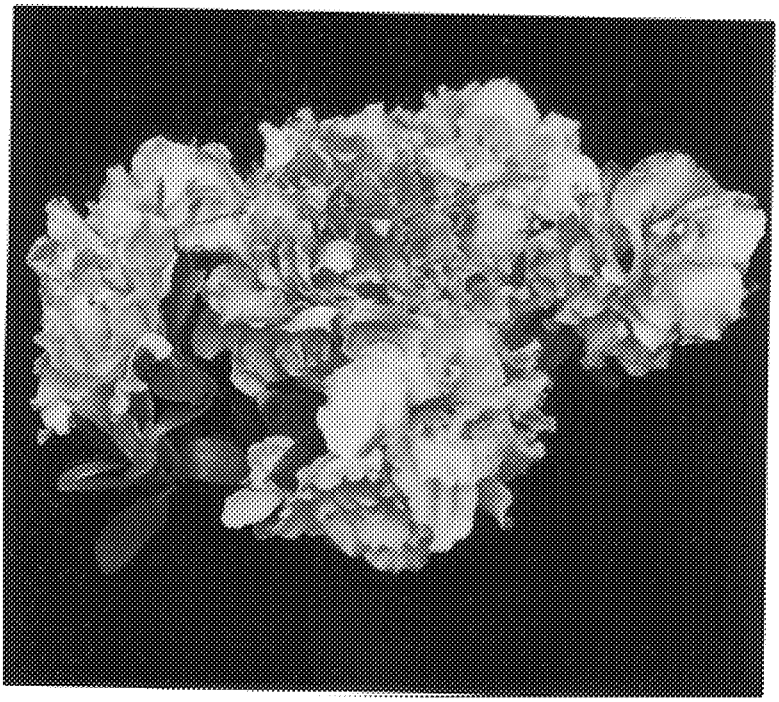

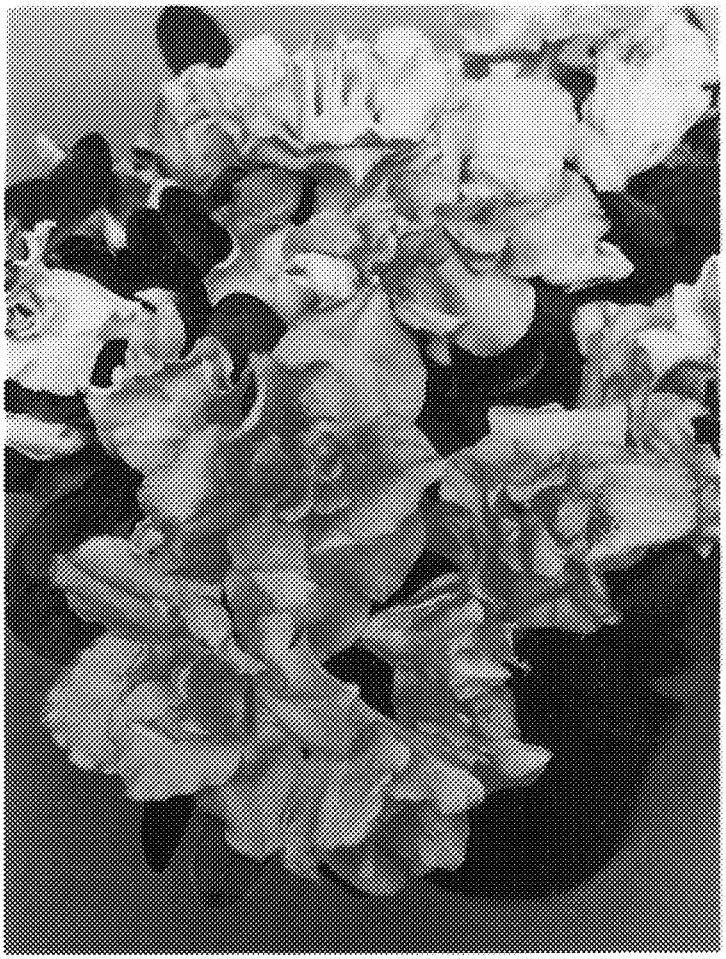

* * * * *